(12) United States Patent
Du et al.

(10) Patent No.: US 7,560,930 B2
(45) Date of Patent: Jul. 14, 2009

(54) MAGNETIC RESONANCE IMAGING APPARATUS FOR SCANNING THE SPINE

(75) Inventors: Jian Jun Du, Shenzhen (CN); Ludwig Kreischer, Dormitz (DE); Jian Zhong Li, Shenzhen (CN); Jian Hua Pei, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/038,962

(22) Filed: Feb. 28, 2008

(65) Prior Publication Data
US 2008/0204023 A1 Aug. 28, 2008

(30) Foreign Application Priority Data
Feb. 28, 2007 (CN) .................. 2007 1 0064089

(51) Int. Cl.
*G01V 3/00* (2006.01)
(52) U.S. Cl. .................. 324/318; 324/322
(58) Field of Classification Search .......... 324/318, 324/322
See application file for complete search history.

(56) References Cited

U.S. PATENT DOCUMENTS 5,696,449 A * 12/1997 Boskamp ............ 324/318
6,946,836 B2 * 9/2005 Kuhara ............... 324/307
7,116,195 B2 * 10/2006 Vittorio .............. 335/216

* cited by examiner

*Primary Examiner*—Louis M Arana
(74) *Attorney, Agent, or Firm*—Schiff Hardin LLP

(57) ABSTRACT

The present invention discloses a magnetic resonance imaging apparatus for scanning a spine, comprising a body coil for emitting signals, a patient table within the body coil and a spine coil for receiving signals, wherein said spine coil is fixed within said body coil and disposed under said patient table. Said patient table is movable within said body coil by slide rails fitted at the two sides thereof, so as to reduce the length of said spine coil. The cross section of said patient table is in an arched shape, and the cross section of said spine coil is in an arched shape which matches that of said patient table. By using the apparatus of the present invention, since the spine coil is disposed underneath the board of the patient table, the design and production of the board of the patient table are simplified, the number of radio frequency choke coils and radio frequency element units is reduced and so are the costs; also, the space for the patient is increased, so the patient's comfort is improved; and furthermore, the repeated plugging and unplugging of the spine coil, as in the prior art, are avoided so as to reduce the probability of damaging the coil.

7 Claims, 2 Drawing Sheets

MAGNETIC RESONANCE IMAGING APPARATUS FOR SCANNING THE SPINE

BACKGROUND OF THE INVENTION

1. Field of the Invention

The present invention relates to a magnetic resonance imaging apparatus, and particularly to a magnetic resonance imaging apparatus for scanning a spine.

2. Description of the Prior Art

Magnetic resonance imaging (MRI) is an imaging technology for obtaining internal structural information of an object by means of the magnetic resonance phenomena. MRI is broadly used in the field of medical imaging due to its significant advantages, such as a large number of imaging parameters, high resolution, tomography in any layer required, non-destructive imaging, etc.

It is normally considered that if a surface coil is close to a patient, the image signal would be strong, the noise level low, the signal-to-noise ratio high, and the images relatively fine. When performing the magnetic resonance imaging on a human spine, a spine coil is usually used in order to obtain magnetic resonance images of relatively high qualities, and this makes it necessary to keep the coil sufficiently close to the human body. As to the spine coil, it is conventionally disposed on the upper surface of a patient table, and the patient lies on the spine coil for carrying out the imaging, as shown in FIG. 1.

FIG. 1 shows a longitudinal structural illustration of a prior art magnetic resonance imaging apparatus for scanning a spine, and FIG. 2 is the lateral structural illustration of the apparatus. In FIGS. 1 and 2, gradient coils 12 are embedded a magnet 11, a body coil 13 is on the inner wall of the magnet 11; a patient table 16 is located within the chamber of the magnet 11, and a spine coil 15 is arranged on the upper surface of the patient table 16. When performing a scan on a patient 14 lying on the patient table 16, actually the patient lies on the spine coil 15. The thickness of the spine coil 15 is usually about 40 to 60 mm.

During the process of scan-imaging, the relative movements between the patient 14 and the spine coil 15 are quite complicated. Therefore, when carrying out the scan, in order to obtain the scanned images of the whole spine of the patient 14 conveniently and promptly, the spine coil 15 is usually set to have a length equal to or slightly longer than the human spine, so that after a patient 14 has laid down on the patient table 16, the scanned image of the whole spine of the patient 14 can be obtained by one go without any movement.

Generally, the magnetic resonance imaging apparatus for scanning a spine in the prior art has following disadvantages:

1) the relative movement between the patient and the spine coil is impossible, so the spine coil needs to have a sufficient length in order to achieve the scan of a whole human spine, therefore the coil needs to use a large number of radio frequency component units, which lead to high costs;

2) as shown in FIG. 2, since there is the spine coil between the patient and the patient table, it leads to the reduction of the distance HI between the inner wall of the upper part of the emitting body coil and the patient, resulting in a narrow space for the patient, and reducing the patient's comfort; and 3) since there exists certain coupling between the spine coil and the emitting body coil, it is necessary to unplug the spine coil when the apparatus is not in operation and to re-plug it into the corresponding socket for next operation. Such repeated plugging and unplugging increases the probability of damaging the coil, and therefore affects the reliability of the coil and the imaging quality of the apparatus.

Currently, a common solution is to embed the spine coil into the board of the patient table, but by doing so the structural complexity of the board of the patient table is increased, and at the same time during its use the coil is still subject to factors such as the patient's body weight, etc., so the problem regarding vulnerability to damage still exists.

SUMMARY OF THE INVENTION

An object of the present invention is to provide a magnetic resonance imaging apparatus for scanning a spine, in which by changing the position for fitting the spine coil the patient's space is increased so as to improve the patient's comfort, and by reducing the number of radio frequency components in the spine coil the equipment costs are reduced.

In order to solve the aforementioned technical problem, the present invention provides a magnetic resonance imaging apparatus for scanning a spine, having a body coil for emitting signals, a patient table within the body coil and a spine coil for receiving signals, wherein the spine coil is fixed within the body coil, and disposed underneath the patient table.

In the apparatus of the present invention, the patient table is movable within the body coil by means of slide rails fitted at two sides thereof. Since the scan-imaging of the patient can be performed by moving the patient table, the length of the spine coil can be reduced.

In the apparatus of the present invention, the patient table has an arced shape, and the cross-section of the spine coil has an arced shape that matches that of the patient table, so as to make the distance between the patient table and the spine coil less than or equal to 3 mm.

In the apparatus of the present invention, since the spine coil is located underneath the patient table, the spine coil can be connected by a signal line under the patient table directly to the control system of the magnetic resonance imaging apparatus.

Compared with the prior art, with regard to ensuring a good signal-to-noise ratio of the spine coil, the present invention has the following features:

1. With the spine coil disposed underneath the board of the patient table, the design of the board of the patient table is simplified, which is advantageous for manufacturing and reducing the costs.

2. By increasing the distance between the upper side inner wall of the body coil and the patient, the space for the patient in the emitting body coil is increased, and the patient's comfort is improved.

3. By connecting the signal line under the patient table directly to the control system, the number of RF (radio frequency) chokes is reduced, which further reduces the costs.

4. Since the spine coil is fixed within the emitting body coil, it avoids the repeated plugging and unplugging of the spine coil as in the prior art, so the probability of damaging the coil is reduced, and the reliability of the coil is guaranteed.

5. The number of radio frequency component units in the spine coil is reduced, because the scan of a whole spine can be preformed by moving the patient table, so the costs are further reduced.

DESCRIPTION OF THE PREFERRED EMBODIMENTS

The primary basis of the present invention is to move the spine coil from the upper surface of the patient table or the interior of the board of the patient table to beneath the patient table, so as to solve the problems, such as the narrow space and high equipment costs in the prior art caused by disposing the spine coil on the upper surface of the patient table or embedding the same into the board of the patient table.

One manner for realizing the magnetic resonance imaging apparatus for scanning a spine of the present invention is to fix the spine coil directly on the lower surface of the board of the patient table. Compared with the prior art, this does not change the length of the spine coil, and it only changes the fitting position of the spine coil. However, after having fitted the spine coil to the lower surface of the board of the patient table, the distance between the inner wall of the body coil above the patient table and the patient is increased, so the patient's comfort is improved. In addition, since there is no longer a spine coil on the upper surface of the patient table or within the board of the patient table, the patient table can be designed as thin as possible, so as to enable the spine coil to still achieve a preferred signal-to-noise ratio.

Figure 1:
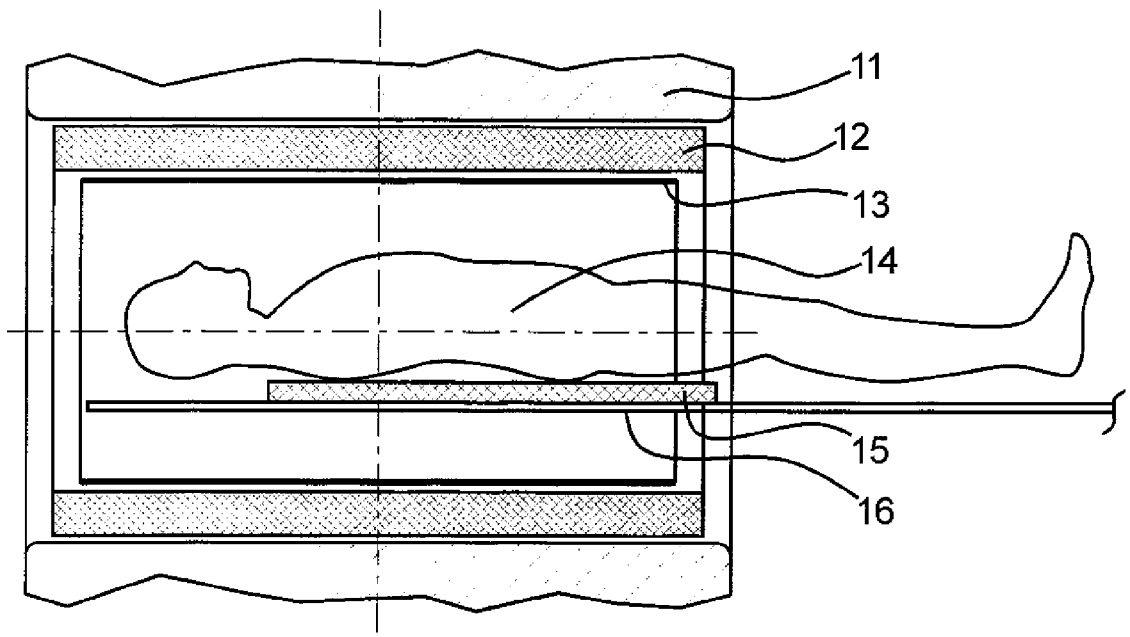
FIG. 1 is a longitudinal structural illustration of a prior art magnetic resonance imaging apparatus for scanning a spine.
Figure 2:
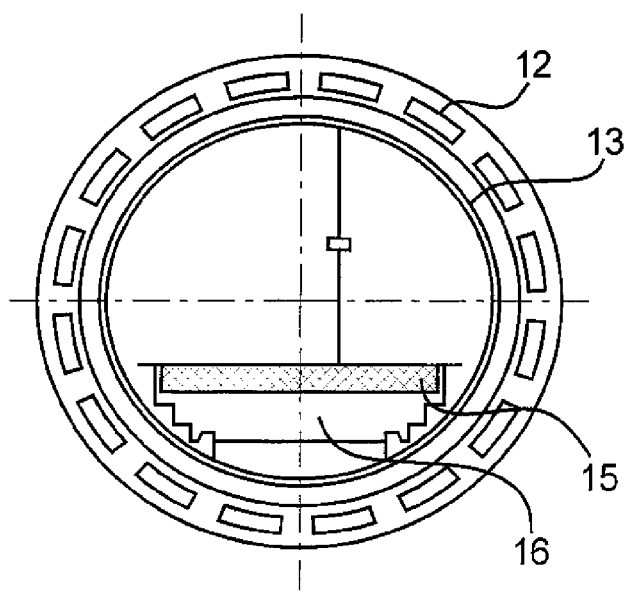
FIG. 2 is a lateral structural illustration of a prior art magnetic resonance imaging apparatus for scanning a spine.
Figure 3:
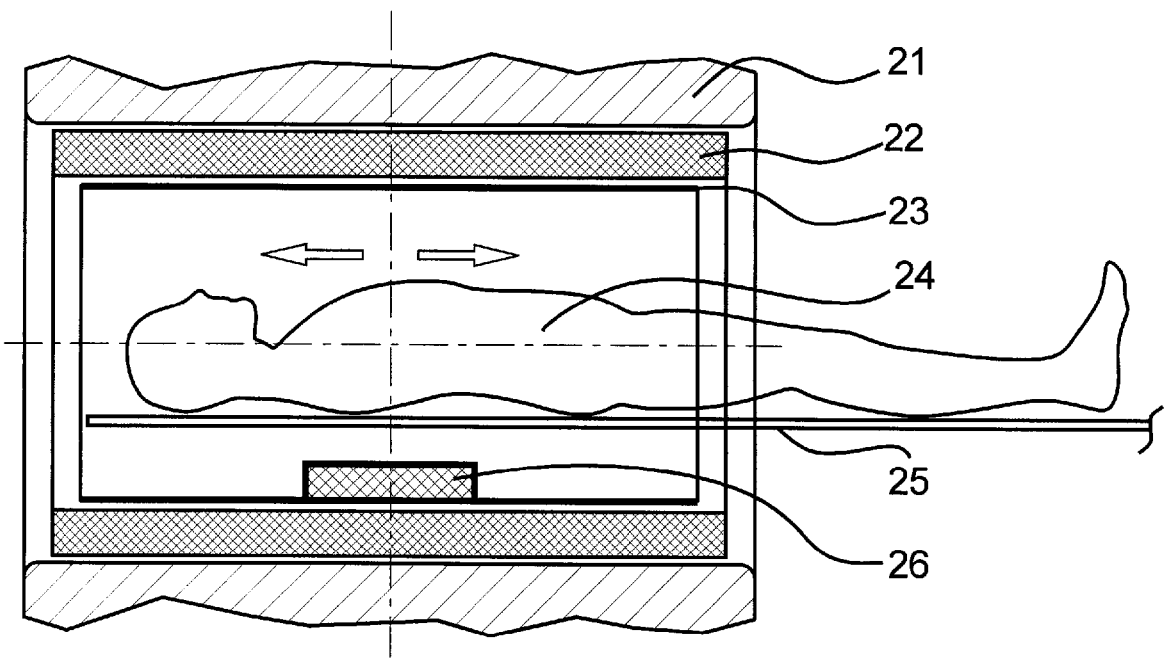
FIG. 3 is a longitudinal structural illustration of an embodiment of the present invention.
Figure 4:
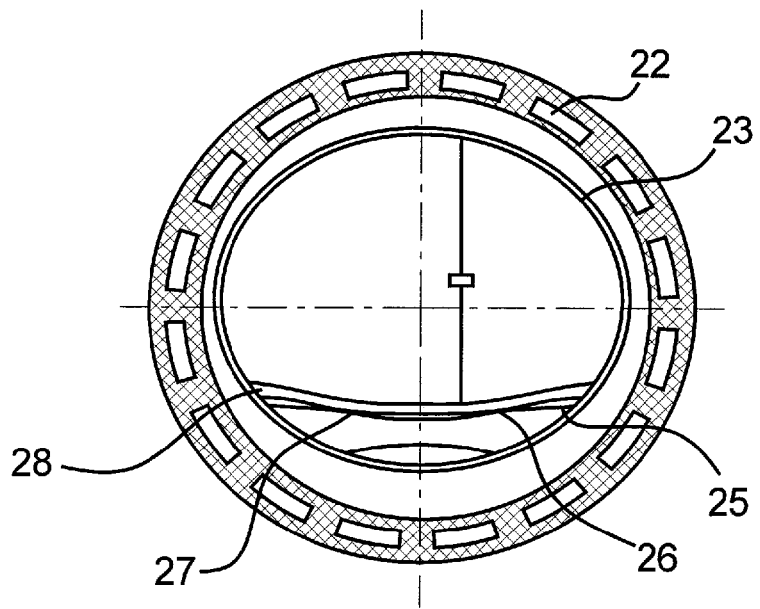
FIG. 4 is a lateral structural illustration of the embodiment of the present invention.

A preferred manner for realizing the magnetic resonance imaging apparatus for scanning a spine of the present invention is to fix the spine coil on the inner surface of the emitting body coil underneath the patient table, as shown in FIGS. 3 and 4. The magnetic resonance imaging apparatus in this preferred realization manner proposed in the present invention mainly comprises: a magnet 21 embedded with gradient coils 22, a body coil 23 for emitting signals on the inner wall of the magnet 21; a patient table 25 and a spine coil 26 located underneath the patient table 25 for receiving the signal, both within the body coil 23. In addition, the relative movements between the patient table 25 and the spine coil 26 are realized by way of slide rails 28 at two sides the patient table.

In this preferred realization manner of the present invention, the spine coil 26 is disposed directly underneath the board of the patient table 25, and fixed on the inner surface of the body coil 23. This increases the distance H2 between the inner wall of the upper body coil 23 above the patient table and the patient 24, and improves the comfort of the patient 24 lying on the patient table 25. Moreover, by reducing as much as possible the distance between the spine coil 26 and the patient 24, it also ensures that the signal-to-noise ratio of the spine coil 26 can reach to the level of or even become better than the signal-to-noise ratio of the spine coil in the prior art.

Currently in the prior art, after a patient lying on the patient table has reached predetermined position, he or she will not move any more, and the magnetic resonance images are then obtained by the spine coil of a length capable of scanning the whole human spine in one pass. In the preferred realization manner of the present invention, since the spine coil 26 is disposed underneath the patient table 25, compared with the prior art in which the patient lies on the spine coil, this spine coil and the spine part of a patient can have relative movements, and the patient's whole spine is scanned by moving the patient table during the scan-imaging process. Within the body coil 23 in FIG. 3, the two arrows above the patient 24 indicate that the patient lying on the patient table 25 can have movements relative to the spine coil 26. The free movements of the patient table 25 are realized by the slide rails 28 fitted at two sides of the patient table 25, as shown in FIG. 4.

Since the patient 24 lying on the patient table 25 and the spine coil 26 can conveniently have relative movements during the scan-imaging process, and furthermore the imaging quality and operating efficiency are not affected, it can be designed and manufactured with a reduced number of radio frequency components 27 in the spine coil 26, so as to further reduce the equipment costs. As shown in FIGS. 3 and 4, compared with the prior art, in the preferred realization manner of the present invention, the length of the spine coil 26 is less than that of the patient table 25, and its length is reduced at least to a half of that of the prior art, or even further less, as long as it meets the minimum size of an imaging area. When performing the scan-imaging on the spine of the patient 24, the scan of the whole pine of the patient 24 is realized by the slide rails 28 for moving the patient table 25 thereon.

In order to improve the signal-to-noise ratio of the spine coil 26 by reducing as much as possible the distance between the spine coil 26 and the patient 24, in the preferred realization manner of the present invention, the patient table 25 is designed and made as thin as possible. As shown in FIG. 4, the cross-section of the patient table 25 in the present invention is in an arced shape, and in order to reduce the distance between the spine coil 26 and the patient table 25, the cross-sectional shape of the patient table 25 is designed and made into an arced shape which matches the external shape of the spine coil 26, and the curvature thereof matches that of the spine coil 26. According to the prior art, it is possible to achieve that the distance between the lower surface of the patient table 25 and the upper surface of the spine coil 26 is less than or equal to 3 mm, and it meets the requirement to the minimum distance that allows the spine coil 26 not to affect the movements of the patient table 25. Since the spine coil is no longer disposed on the upper surface of the patient table 25 or within the board of the patient table 25, the thickness thereof can be reduced as much as possible to make it even thinner, and its cross-section design can be simpler, so as to reduce the equipment costs. In this way, the arc-shaped board avoids the loss of the radio frequency signals firstly by matching the arched shape, secondly by reducing as much as possible the distance between the spine coil 26 and the patient 24; and these two points would be able to ensure as much as possible that the signal-to-noise ratio of the spine coil 26 reach or even become better than the signal-to-noise ratio of the spine coil in the prior art.

Since in the preferred realization manner of the present invention, the spine coil 26 is shifted from the upper side of the patient table or the interior of the table board to underneath the patient table 25, the spine coil 26 of the embodiment of the present invention as shown in FIGS. 3 and 4 can be connected directly by a signal line under the patient table 25 to a control system of the magnetic resonance imaging apparatus. Compared with the prior art in which the signal cable for external connection of the spine coil 26 passes the center of the magnet and therefore it needs more RF choke coils, while in this realization manner the signal cable for external connection of the spine coil 26 is connected underneath the patient table 25 directly to the system and it no longer passes the center of the magnet. Therefore, the number of the RF choke coils needed can be reduced, so as to further reduce the costs.

In the prior art, since there exists certain coupling between the spine coil and the emitting body coil, it is necessary to unplug the spine coil when the apparatus is not in operation and to insert the plug into the corresponding socket for next operation. Since in the present invention the spine coil is fixed within the emitting body coil, it is not necessary to unplug the spine coil when the apparatus is not in operation. This avoids the repeated plugging and unplugging of the spine coil, makes it more convenient for the operator, reduces the probability of damaging the coil, and furthermore it ensures the reliability of the coil.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance apparatus comprising:
   a patient table configured to receive a patient thereon;
   a magnetic resonance scanner having an opening configured to receive said patient table therein with the patient thereon, said magnetic resonance scanner comprising a basic field magnet that generates a static, homogenous basic magnetic field in an examination volume within said opening, a gradient coil system that generates at least one gradient magnetic field in said examination volume, a whole-body coil that emits radio-frequency signals into the examination subject within said examination region to cause magnetic resonance signals to be emitted from the subject, and a spine coil configured for placement in proximity to the spine of the subject to receive magnetic resonance signals from the spine; and
   said spine coil being mounted within said scanner at a fixed and immovable position relative to said whole body coil and being disposed beneath and separated from the patient table.

2. A magnetic resonance imaging apparatus as claimed in claim 1 wherein said patient table is movable within said whole body coil in said opening.

3. A magnetic resonance imaging apparatus as claimed in claim 2 wherein said patient table comprises slide rails respectively at opposite longitudinal sides of said table that allow movement of said patient table within said whole body coil in said opening.

4. A magnetic resonance imaging apparatus as claimed in claim 3 wherein said spine coil has a longitudinal length that is less than a longitudinal length of said patient table.

5. A magnetic resonance imaging apparatus as claimed in claim 1 wherein said patient table has an arced shape, and wherein said spine coil has a cross-section with an arced shape conforming to the arced shape of said patient table.

6. A magnetic resonance imaging apparatus as claimed in claim 1 wherein said spine coil is located at a distance from said patient table that is less than or equal to 3 mm.

7. A magnetic resonance imaging apparatus as claimed in claim 1 comprising a signal line connected to said spine coil and proceeding under said patient table to a terminal location outside of said whole body coil, said signal line conducting electrical signals from said spine coil to said terminal location.

* * * * *